US006491641B1

(12) United States Patent
Rasmussen

(10) Patent No.: US 6,491,641 B1
(45) Date of Patent: Dec. 10, 2002

(54) APPARATUS AND METHODS FOR ACOUSTIC RHINOMETRY

(75) Inventor: Steen Brabrand Rasmussen, Lynge (DK)

(73) Assignee: Rhinometrics A/S, Lynge (DK)

( * ) Notice: Subject to any disclaimer, the term of this patent is extended or adjusted under 35 U.S.C. 154(b) by 0 days.

(21) Appl. No.: 09/744,396
(22) PCT Filed: Jul. 26, 1999
(86) PCT No.: PCT/DK99/00419
§ 371 (c)(1),
(2), (4) Date: Jan. 24, 2001
(87) PCT Pub. No.: WO00/06019
PCT Pub. Date: Feb. 10, 2000

(30) Foreign Application Priority Data

Jul. 27, 1998 (DK) .................................. PA 1998 00980

(51) Int. Cl.$^7$ ................................................ A61B 5/28
(52) U.S. Cl. ....................................... 600/529; 600/587
(58) Field of Search ................................ 600/533, 529, 600/407, 437, 453, 459, 462, 463, 433, 449, 587

(56) References Cited

U.S. PATENT DOCUMENTS

| 4,326,416 A | 4/1982 | Fredberg |
| 5,316,002 A | 5/1994 | Jackson et al. |
| 5,882,314 A | 3/1999 | Fredberg et al. |
| 5,902,237 A | 5/1999 | Glass |

*Primary Examiner*—Max Hindenburg
*Assistant Examiner*—Pamela L Wingwood
(74) *Attorney, Agent, or Firm*—Dykema Gossett Pllc

(57) ABSTRACT

The invention relates to an apparatus for measuring cross sections in a patient's right and left nose cavity in the cavity behind the nose separation (epipharyn), and in the throat (oropharynx), and for detecting the opening of the Eustachian tube. The apparatus comprises an electro-acoustic sound emitter, a first transmission tube leading from the emitter to a first connecting piece, connecting means for connecting the first connecting piece to a patient's one nostril, a proximal microphone located adjacent the emitter and/or a first microphone built into the first connecting piece, and a computer for generating electrical signals for the emitter and for sampling and analyzing electrical signals from the microphone or microphones. According to the invention the apparatus further comprises a preferably releasable second acoustic transmission tube leading from the emitter in an opposite direction of the first acoustic transmission tube, hereby constituting an elongation of this pass the emitter. The invention further relates to a method for measuring the above-mentioned cross sections.

12 Claims, 9 Drawing Sheets

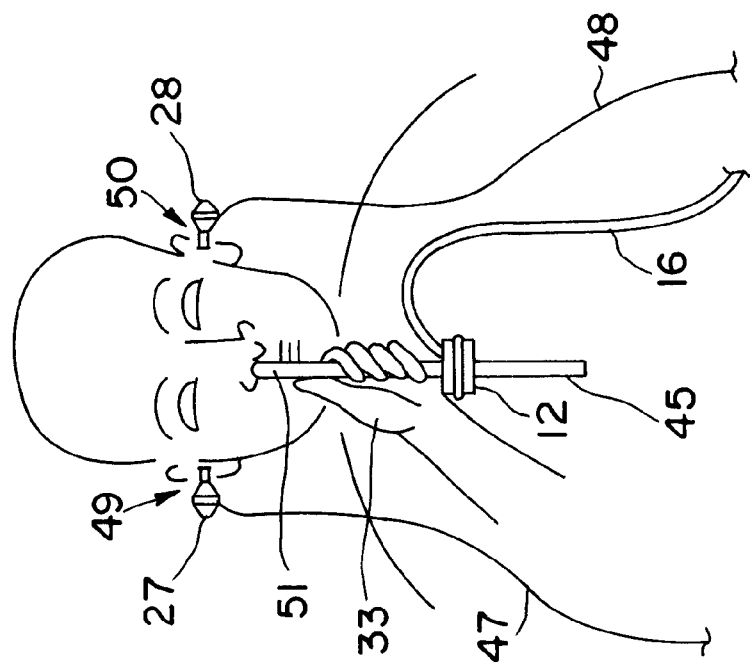
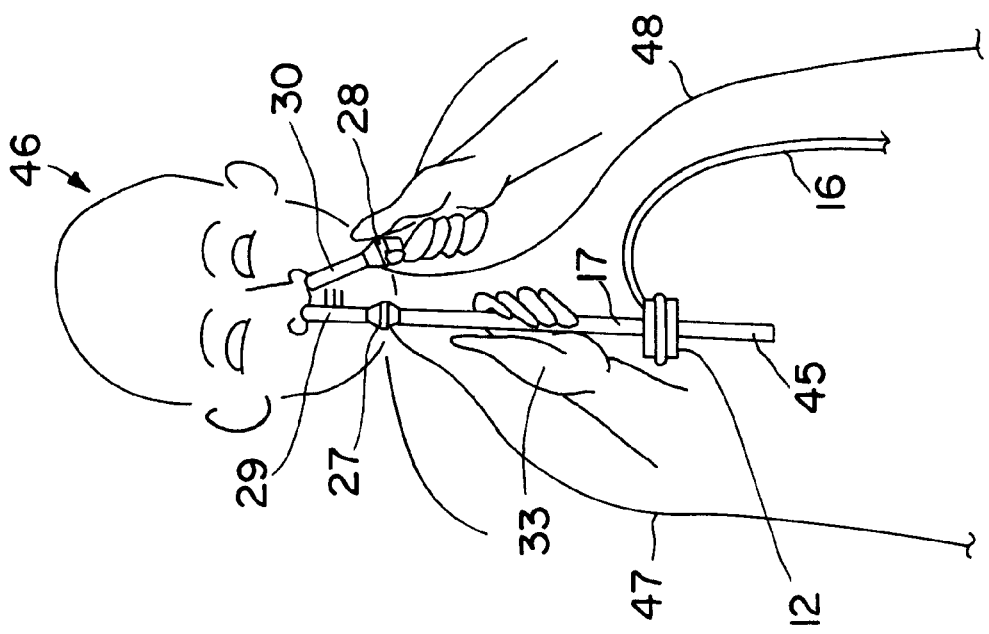

APPARATUS AND METHODS FOR ACOUSTIC RHINOMETRY

FIELD OF THE INVENTION

The invention relates to measuring by acoustics, lengths and cross sections in a patient's right and left nose cavity which are mutually separated by the nose separation (septum nasi), in the cavity behind the nose separation (epipharynx) and in the throat (oropharynx); the invention further relates to detecting the opening of the Eustachian tubes.

BACKGROUND OF THE INVENTION

Acoustic rhinometry (Reflectometry) is, e.g. known from U.S. Pat. No. 4,326,416 (Fredberg). The method and apparatus is further described by Ole Hilberg, Ole Finn Petersen and A. C. Jackson in 1988. An instrument for acoustic rhinometry is produced by the firm Hood Labs in Boston from the beginning of the 1990's and by the Scottish firm GM instruments since 1993. The known methods and apparatuses comprise both the use of continuous and discontinuous signals.

An overview of acoustic rhinometry and known examination methods is found in "Akustisk rhinometri" by Per Djupesland, Tidsskrift for Den Norske Laegeforening, no. 26 1996, 116, pp. 3111–3114.

In acoustic rhinometry (reflectometry) a sound signal is generated and sent into the nose cavities through an adapted connecting piece. Part of the sound signal is reflected from the cavities in the nose and the throat, and by data analysis of the differences between the ingoing and the reflected sound picture. The cross sections are visualized on a screen or a print-out as a function of the distance from the nose opening.

Acoustic rhinometry is suitable for illustrating physiology of the nose mocous membrane, more specifically the thickness of this, for documenting diverting anatomy or for exposing of allergens and other material which irritates the respiratory passages, and for surveying the function of operative or medical treatment. The method can furthermore be used on children and even newborns.

The hitherto known measuring systems for acoustic rhinometry use a technique where a long rigid tube with a sound transducer such as a spark plug located in one end of the tube functions as a sound emitter, generating a planar acoustic wave propagating against the end of the tube which is terminated in a nose adaptation piece for connecting to the patients nostrils. A microphone located somewhere else in the tube measures the generated wave as well as a reflected signal. These rigid tubes normally have a diameter of 12–16 mm and a length of between 30 cm and 2 m.

The reflections in the lung cavities and the nose cavities following changes in the impedance (changes of cross sections) are sampled by the microphone in the tube and are transmitted to a signal processing unit, which calculates the cross sections of the cavities based on these.

Furthermore an equipment with a continuous acoustic broad band spectrum is manufactured and sold by the applicant (formerly S. R. Electronics ApS (DK)).

By means of the above-mentioned technique it is not possible to measure correctly the cross sections further in the respiratory passages of the patient than the rear end of the nose separation as the opposite nose cavity end at this location, whereby a cross section corresponding to the parallel connected acoustic impedance of the opposite nose cavity will be added to the cross section behind the nose separation.

For determining the length of the nose separation an endoscope, CT- or MR scanning, or a simple hook, which is inserted into the, nostril and is lead to the rear surface of the nose separation with the hook behind the edge, whereafter it is pulled back, has hitherto been used. When the hook abuts the rear surface of the nose separation, the examiner will at the nose opening mark the position on the shaft and the hook is retracted; the distance from the hook top to the marking indicated the length of the nose separation. The latter method is unpleasant for the patient and the first mentioned are expensive and implies some risk.

By using the apparatuses and methods for acoustic rhinometry described in the introduction, the length of the nose separation can be determined as the-distance where the sounds from one side of the nostril are identical as measured through the right and the left nostril, respectively (i.e., where the impedance by measuring in the right and the left nostril, respectively, are identical in the time-domain), but this method is implicit and the result depends of a subjective interpretation of the printed or shown curves. The measuring result is therefore connected with a large uncertainty.

It is an object of this invention to provide an apparatus which, in different configurations, can realize: measuring of cross sections of a patient's respiratory passages, even beyond the termination of the nose separation, measuring of the total cross section of a patient's right and left nose cavity in the same measurement, a simple and reliable measurement of the length of the patient's nose separation, and a simple and reliable detecting of the opening (of) the patient's Eustachian tube.

SUMMARY OF THE INVENTION

By means of the invention an apparatus is achieved which can emit sound signals in two directions along separate transmission tubes. At the sound emitter the two transmission tubes are located in line, which provides symmetrical impedance and reflection conditions.

By the fact that the apparatus hereby can send sound signals along two transmission tubes, a possibility for applying the sound signal (two) both nostrils of the patient is achieved, whereby both nose cavities takes part in the cross section measurement. This gives in one operation more valuable measurement and eliminates the harmful effect of the one nose cavity, which is not measured, acting as an acoustic shunt impedance (see above) on the second nose cavity and the cavity behind the rear edge of the nose separation.

The mentioned symmetrical impedance and transmission conditions ensures that the two part signals which propagates along respective nose cavities are sufficiently concordant for adding to a common signal at the nose separation rear edge without being distorted, which would deteriorate or destroy the measurement of the respiratory passages beyond the nose separation rear edge.

If the second transmission tube is releasable, the apparatus can still be used as the known apparatuses for rhinometry, for measuring through one nostril and for the mentioned measurement of the length of the nose separation and for detecting opening of the Eustachian tube.

With the features mentioned in claim 2 a simple and reliable connection to the patient's nostril is achieved. If the microphones are located in the termination pieces, a considerable possibility for registration of the course of the cross section in each nostril and each nose cavity separately, still preserving the possibility of registration of the respiratory passages behind the termination of the nose separation.

With the features mentioned in claim 3 and 4 a particularly convenient configuration of the apparatus, when only the first transmission tube is used, having very limited risk of undesired reflections.

With the features mentioned in claim 5 a possibility is achieved for using the apparatus for measurement of the length of the nose separation.

With the features mentioned in claim 6 a possibility is achieved for using the apparatus for detecting opening of the Eustachian tube.

With the features mentioned in claim 7 an advantageous connection of the sound emitter to the transmission tubes is achieved.

It is a second objective of the invention to provide methods for the measurements and detections.

With the features mentioned in claim 8 it is achieved that the first acoustic signal propagates at the same time through both nostrils of the patient as two identical signals which therefore are identical at the rear edge of the nose separation, wherefore they will be added to a common well defined signal which propagates further into the patients respiratory passages and make rhinometry measurement possible in these respiratory passages located beyond the nose separation rear edge.

With the features mentioned in claim 9 a simplification of the apparatus and the computer software, which performs the signal analysis, is achieved.

With the features mentioned in claim 10 a more precise measurement is achieved, as the transmission tubes do not form part of the transmission path where the acoustic signals are changed by reflection a.o., and that the patients two nostrils and nose cavities are measured separately, whereby differences in the two sides can be seen and analyzed.

With the features mentioned in claim 11 a simple and reliable measurement of the length of the patients nose separation is achieved, without any discomfort.

With the features mentioned in claim 12 a very simple and reliable way of detecting whether a patients Eustachian tube is open or closed is achieved. As according to the invention only needs to be connected apparatus to the patient's ears and nostrils, the detecting can be performed as the patient eats or drinks or swallows.

The apparatus may be constituted by a known apparatus, which has been provided with a supplementary tube and with a correspondingly revised signal processing software. The invention also relates to such supplementary equipment, which may be manufactured and marketed separate from the complete apparatus.

The invention is in the following be explained more detailed by means of embodiments with reference to the drawings on which the same references refer to corresponding parts on all figures.

BRIEF DESCRIPTION OF THE DRAWINGS

FIG. 11 schematically shows the use of the apparatus in FIG. 7 at measuring the length of the nose separation on a patient, and FIG. 12 schematically shows the use of the apparatus in FIG. 7 at the detecting of opening of the Eustachian tube of a patient.

DESCRIPTION OF THE PREFERRED EMBODIMENT

An equipment of the type described in the introduction, where a continuous broad band spectrum is used, has been manufactured and sold by the applicant since 1992 (formerly S. R. Electronics ApS (DK)).

Figure 1:
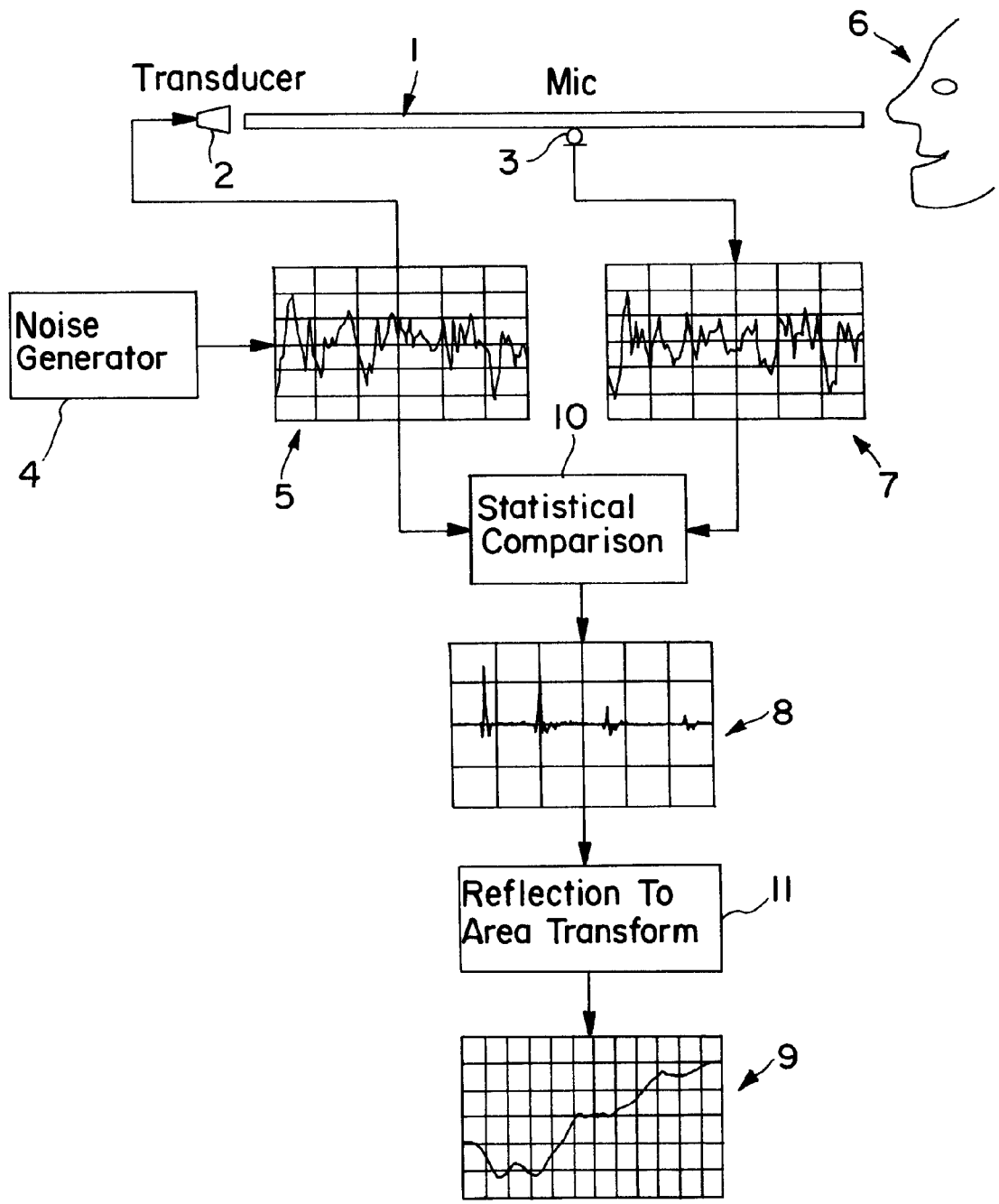
FIG. 1 schematically shows the construction and use of a known apparatus for rhinometry.
Figure 2:
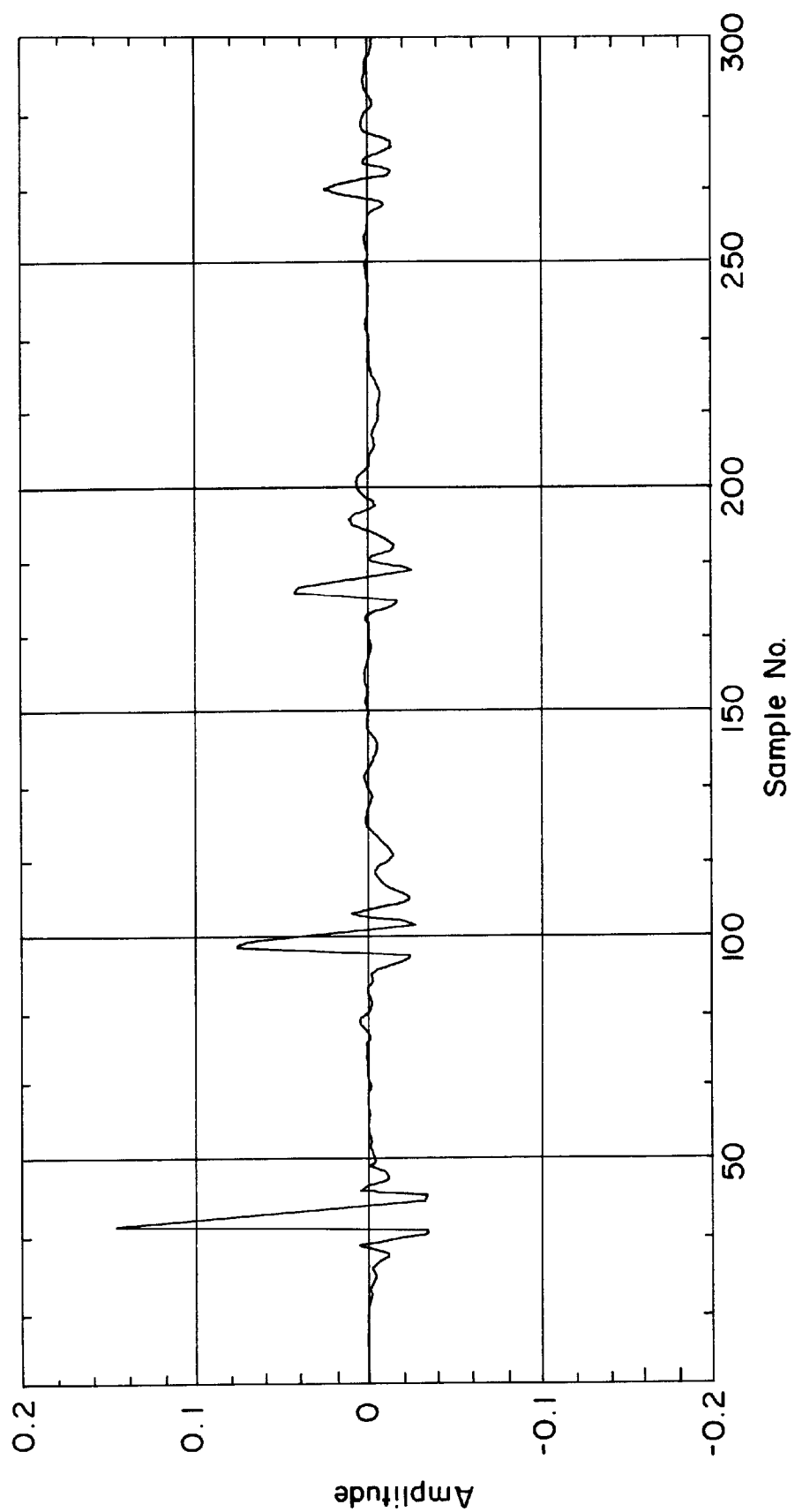
FIG. 2 in an enlarged view shows the impulse-response curve in FIG. 1.
Figure 3:
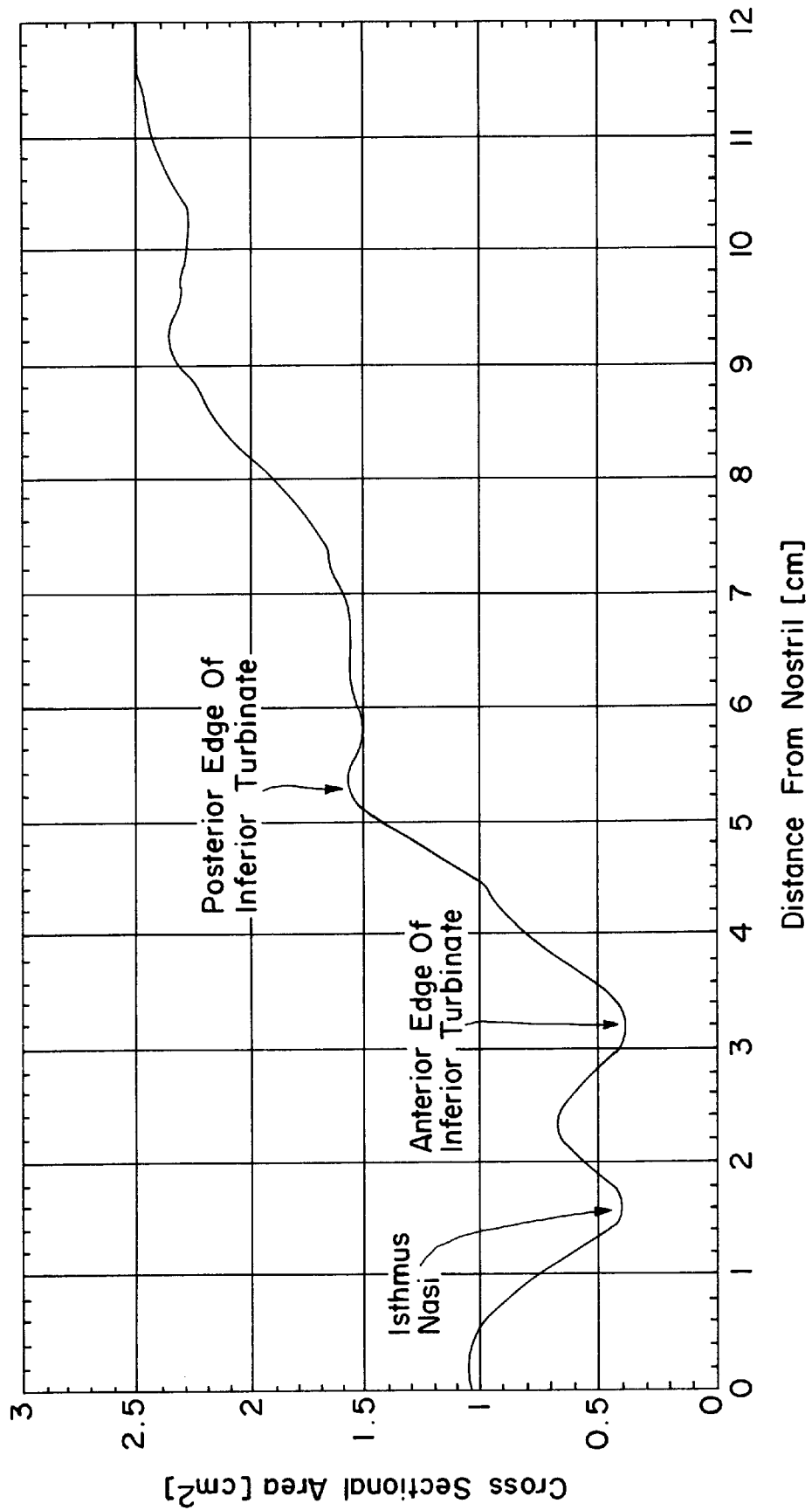
FIG. 3 in an enlarged view shows the curved over the calculated cross section area.

The construction and the use of this known apparatus appears from FIGS. 1–3. In FIG. 1 the described elongate tube 1 appears with the sound emitter 2 and the microphone 3. A digital noise generator 4 emits a continuous white band noise signal 5, which is transferred to the sound emitter 2. The signal 7 reflected from the patient 6 is sampled by the microphone 3.

The signals 5 and 7 are statistically compared by means of a computer 10 with a suitable program and the program generates a reflection signal 8. Based on this the program 11 generates an area curve 9 from a impedance transformation which shows the course of the cross section area of the patient's respiratory passages as a function of the distance.

The reflection signal 8 is shown in a larger scale in FIG. 2 and the area curve 9 is shown in larger scale in FIG. 3. The shown signal 8 and the curve 9 are only examples for illustrating the function of the apparatus.

Figure 4:
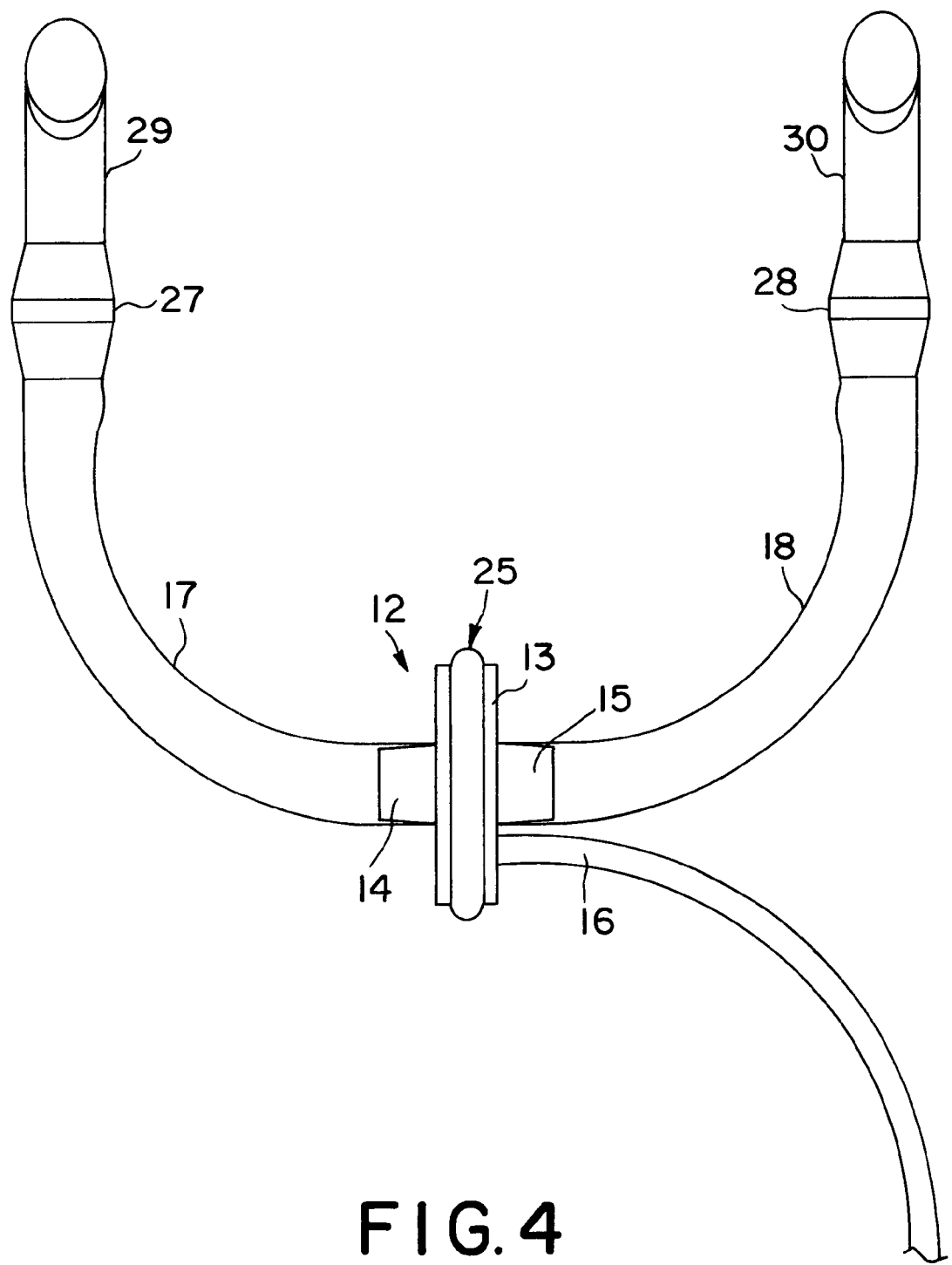
FIG. 4 schematically shows an apparatus according to the invention for measuring the total cross section area of a patient's right and left nose cavity in the same measurement and for cross section measurement of the patients respiratory passages beyond the termination of the nose separation.
Figure 5:
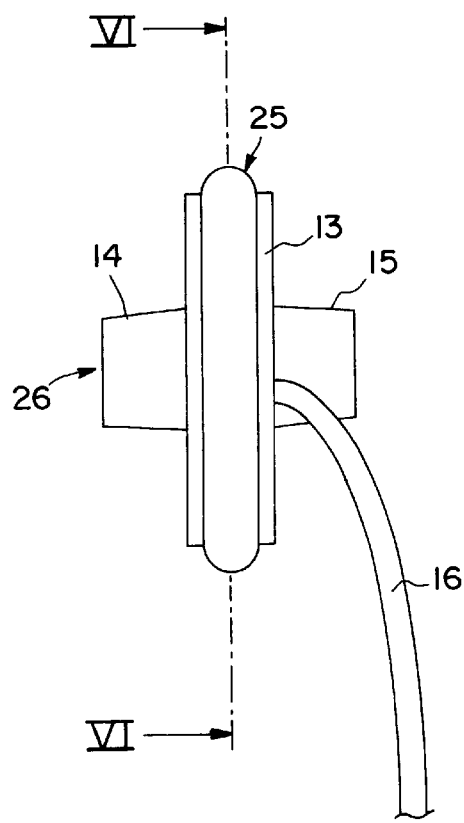
FIG. 5 schematically shows the sound emitter and the microphone part of the apparatus in FIG. 1.
Figure 6:
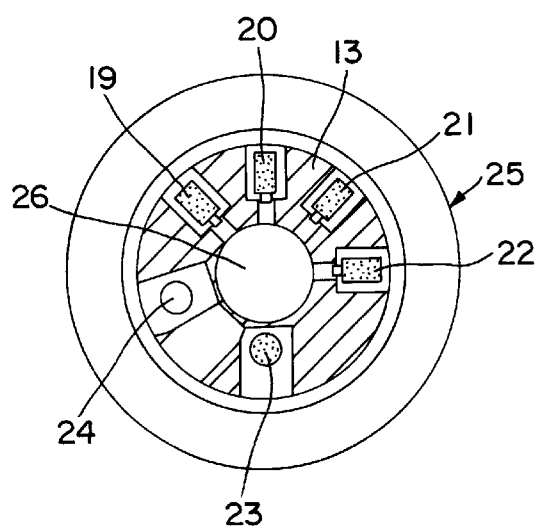
FIG. 6 is a cross section after the line VI—VI in FIG. 5.

The embodiment shown in FIGS. 4–6 for an apparatus according to the invention has a sound emitter unit 12 with a housing 13, e.g., made from aluminum. The housing 13 comprises seven radial bores (FIG. 6) which contain four electro-acoustic transducers 19–22, a microphone 23 and an exit hole 24 for a connecting cable 16 (FIG. 4–5). Through this cable the transducers 19–22 and the microphone 23 are connected to a not shown computer with suitable computer programs for signal processing, statistics and analysis.

The housing 13 is on each side provided with a connecting piece 14–15, between which a central axial bore 26 extends, forming a piece of a transmission tube extending between the connecting pieces 14–15 and at the same time constitutes the cavities of these.

In the continuations of the radial bores towards the central bore 26 there is adjacent each transducer located a discrete acoustic impedance for correct impedance (connection) fitting of the transducers to the acoustic impedance of the transmission tube 26.

The radial bores are closed at their ends and are removed from the central bore 26 by means of a rubber ring 25 which by means of its elasticity is located in a recess on the outer cylindrical surface of the housing 13.

In FIG. 4 it is shown how a first transmission tube 17 in the form of a plastic tube is located on the connecting piece 14 and how a second transmission tube 18 in the form of a similar plastic tube is located on the connecting piece 15. Each of the transmission tubes is terminated with a termination piece 27–28, on each of which a nose piece 29–30 for connecting to a patient's nose is located.

According to the invention the probe 12 constructed symmetrically, such that one or more sound transducers 19–22 (sound emitters) are located in such a manner in the wall, in parallel or in series, that the signal from here is lead to the probe through an acoustic 10 impedance (correction) fitting. The microphone 23 must be located on the same axis.

In the embodiment shown in FIGS. 4–6 the exit of each of the transducers in the tube 26 provided with an acoustic impedance, e.g., of the type Knowles BF-1921. Hereby it is achieved that the total acoustic energy from the transducers is transmitted free of reflection to the measuring probe if such need to be inserted.

The transducer signal will, in the form of planar in phase waves propagate in both directions in the flexible pipes or tubes, which according to the invention are terminated with two nose adaptation pieces 29–30 in the ends.

Figure 9:
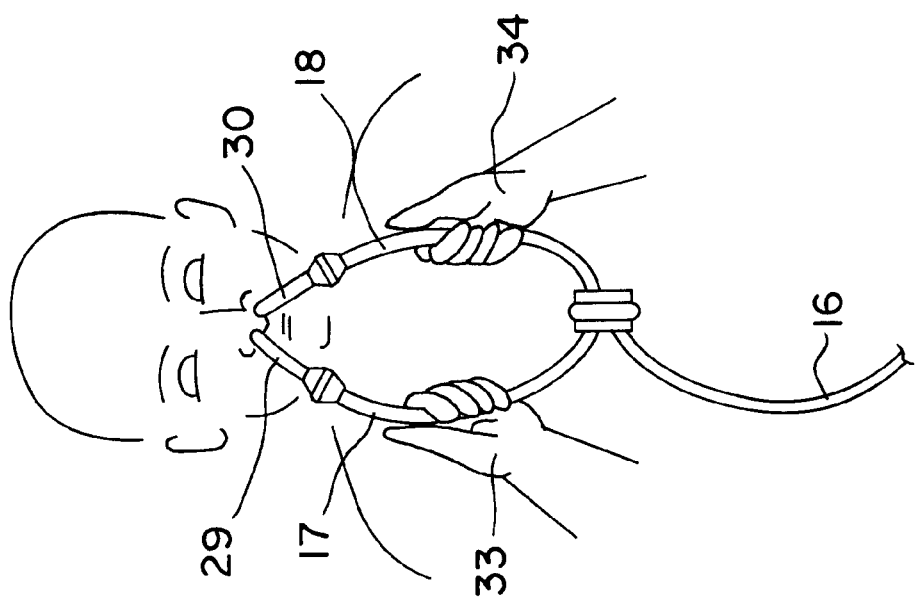
FIG. 9 schematically shows the use of the apparatuses in FIG. 4 and 7 by measurement on a patient.

A typical use of the apparatus in FIGS. 4–6 is shown in FIG. 9. The examiner has fetched the tubes with his hands 33–34 and brought the nose adaptation pieces 29–30 into close contact with the patient's two nostrils.

By connecting the nose adaptation pieces 29–30 to the patient's two nostrils at the same time, the two parts of the sound signal propagate into the nose and the reflections which are created in the patient's two nose cavities prior to the rear edge of the nose separation will create reflections which will propagate back to the microphone 23 through the nose adaptation pieces 29–30 and the tubes 17–18.

Since the reflections from right and left side of the nose will arrive at the microphone at the same distance and at the same time they will be added with prefix. This means that it is the total cross section area of the two nose cavities which is measured at the rear edge of the nose separation, and thereafter (beyond the nose separation) the cross section area of the remaining respiratory passages.

Beyond the rear edge of the nose separation the two planar waves from the transducers 19–22 be added and the reflections which are created beyond this point will be added and propagate back to the microphone, likewise through two symmetrical tubes 17–18. In the microphone point 23 the signals will again be added and the signal processing program in the not shown computer can in this manner process the sum of the signals in a normal manner.

The calculation algorithms can hereby be performed as known from the impedance-to-area-converting of the signals in known apparatuses, in a normal known manner.

The probe 12 is hereby utilized in both directions and a far better measuring accuracy beyond the nose separation is achieved. At the same time it is achieved that the total energy from the measuring transducer is utilized optimally without losses at the opposite end of the probe (as it is the case by the known technique).

Figure 10:
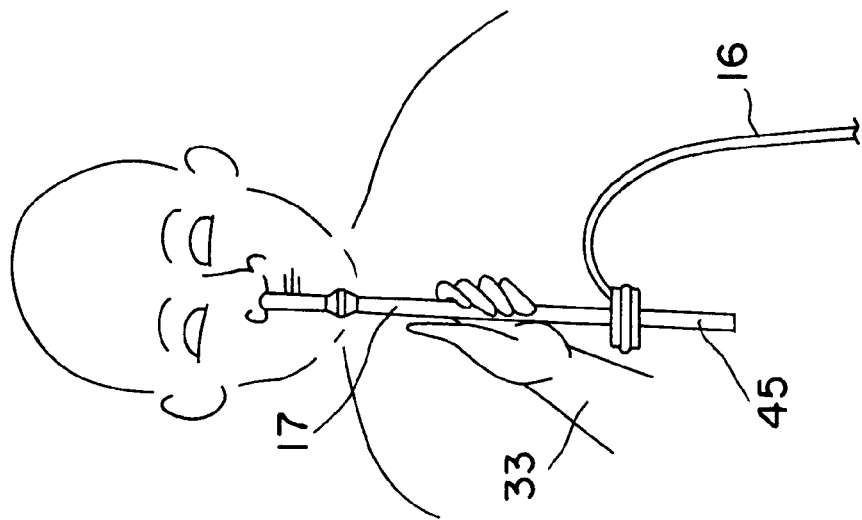
FIG. 10 schematically shows the apparatus in FIG. 4 configured as a known apparatus for rhinometry.

If the user wishes to measure a single nostril separately, one branch, e.g. the tube 18, can be removed from the probe housing 12 and can be replaced by an end piece 45 with an acoustic damping material such that no reflections from here propagates back to the microphone. The software must of course be changed in accordance herewith. This is illustrated in FIG. 10.

The opposite side 18 of the measuring probe 12 can, if provided with a longer tube than the measuring side 17, also be utilized for providing a possibility for respiration or insertion of pH electrodes or the like, during the measurements, as described in DK patent application no. 1304/94. Hereby the described measurements can be performed simultaneously with using a catheter for examination of cavities. Hereby the mapping of the cavities expressed in the area curves 9 may be used in a treatment where utensils must be introduced in the respiratory passages.

Figure 7:
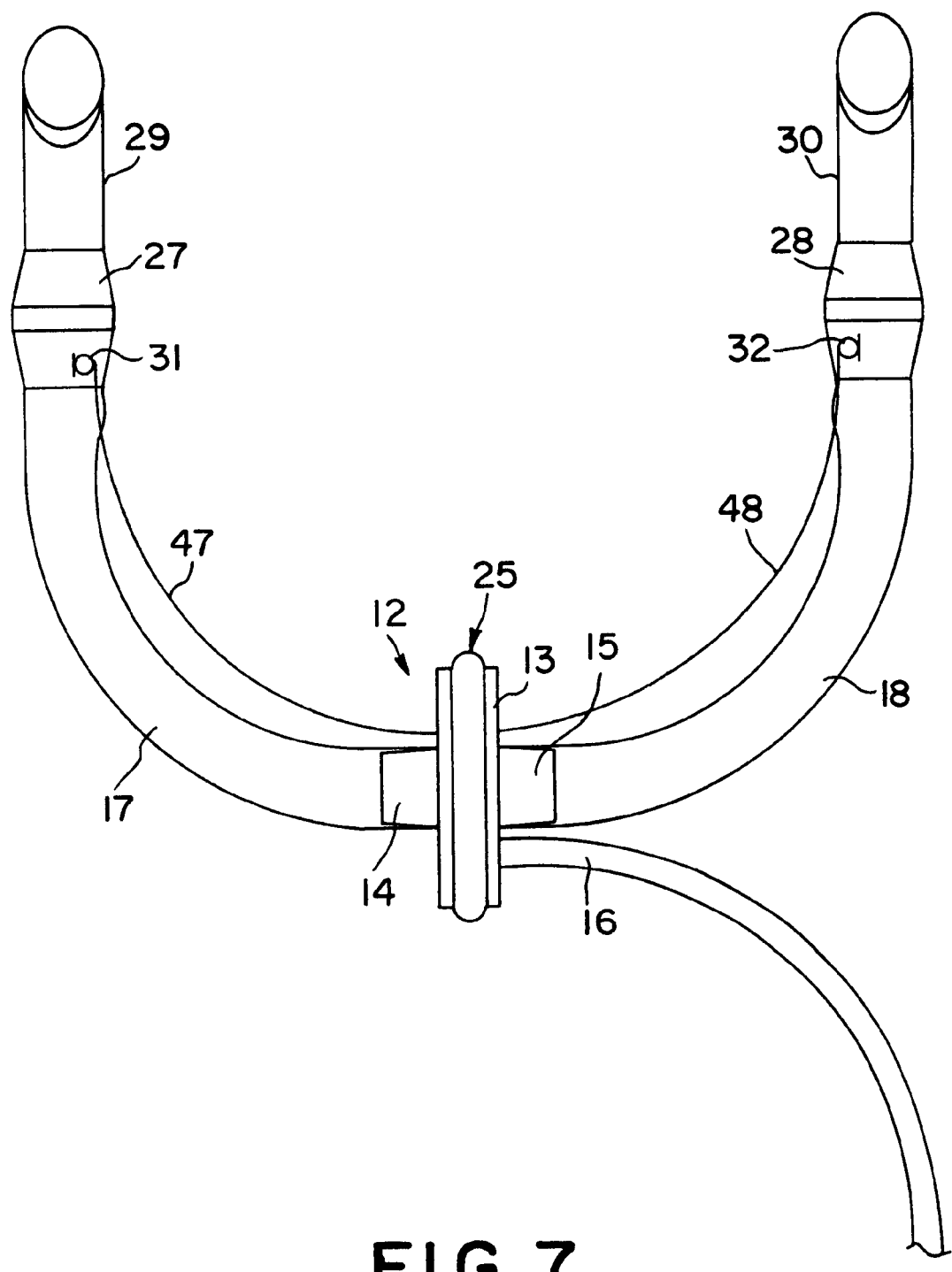
FIG. 7 schematically shows an apparatus according to the invention for simultaneous measuring of both cross section areas of a patient's right and left nose cavity in the same measurement and for cross section measurements of the patient's respiratory passages beyond the termination of the nose separation.
Figure 8:
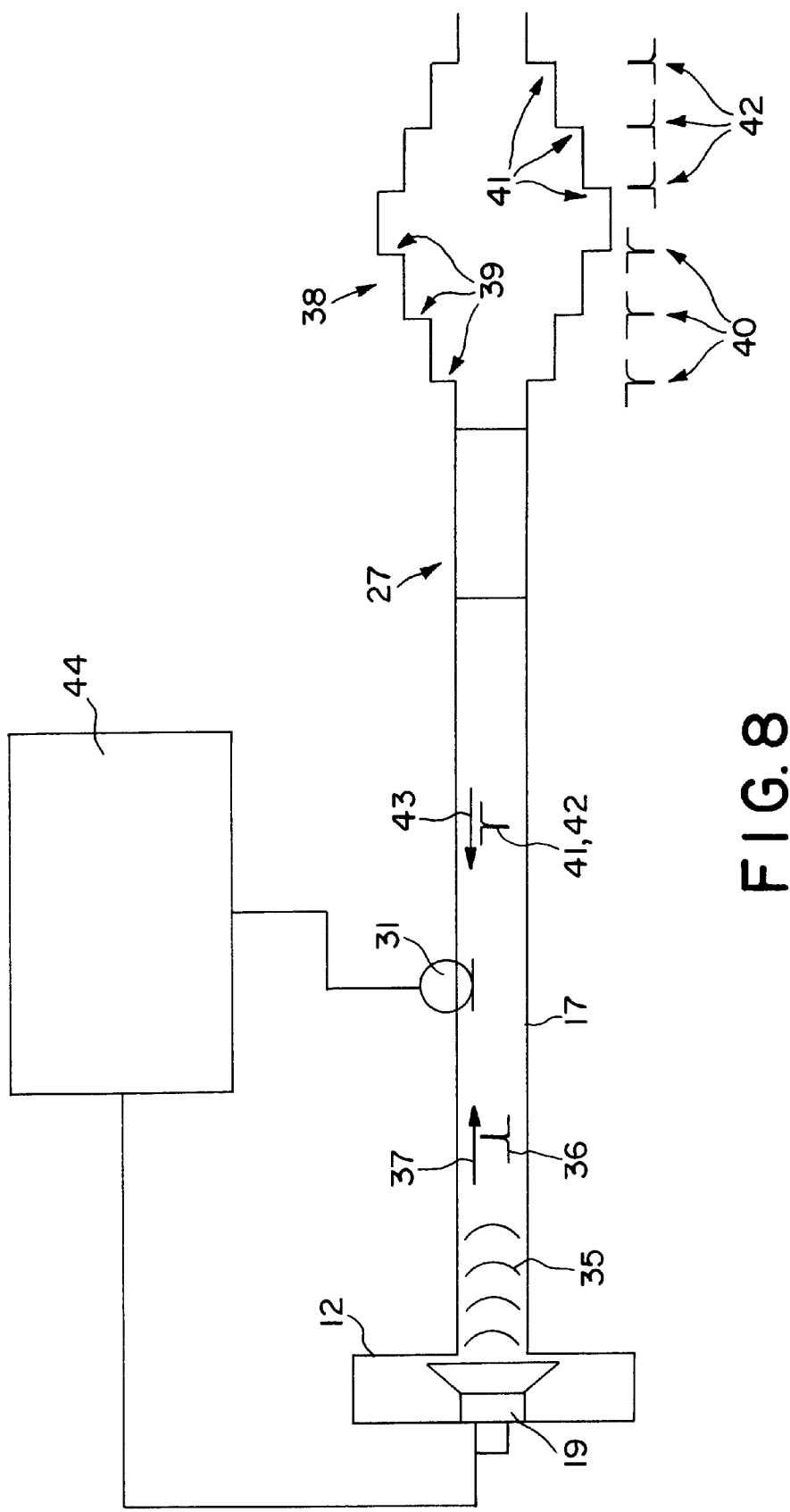
FIG. 8 illustrates the measuring principle in the apparatus of FIG. 7.

In the embodiment of the apparatus according to the invention shown in FIG. 7, the central microphone 23 is substituted by two microphones 31–32, which are located in the transmission tubes 17–18, symmetrically in relation to the sound emitter 19–22. In the embodiment shown the microphones are located in the termination pieces 27–28, while other locations can be used, when only the microphones are located symmetrically in relation to the sound emitter unit 12. The microphones 31–32 are calibrated together and are connected by respective wires 47, 48 to the probe 12.

By constructing the probe with two microphones and adapting the time windows of the measuring system from the two microphones, it is possible to separate reflections from the two nostrils, until the rear edge of the nose separation and to add the sum of the reflections from beyond the rear edge.

By the embodiment in FIG. 7 it is achieved that the two nose cavities are measured simultaneiously. The point where the reflections are identical for the two microphones is an implicit expression for the length of the nose separation. This construction hereby gives a possibility for a simultaneous measurement of the length of the nose separation, which is not possible by means of the prior art.

In FIG, 8 the signal path of the apparatus in FIG. 7 appears schematically. Controlled by a computer 44 with suitable programs, the sound emitter 19 in the sound emitter unit 12 emits a signal 35–36, which propagates in the direction 37 in the tube 17. Via the nose adaptation piece 27 the signal reaches the patient's nose cavity 38. In here cross section enlargements 39 in distance from the sound emitter give rise to reflections of one kind 40 and reductions 41 of the cross section in distance from the sound emitter give rise to reflections of another kind 42. The reflections 41,42 moves back through the tube 17 in the direction 43 and are sampled by the microphone 31. The signal is from here lead to the computer 44, where it is processed as previously described.

An alternative way to use the probe in FIG. 7 for measuring the length of the nose separation comprises letting the system control the run time for an impulse between the two microphones 31–32. This situation is shown in FIG. 11. The acoustic signal path in the one 18 of the tubes of the probe 12 is closed with a special end piece 45 (FIG. 10), as described above).

The system must hereinafter be zero calibrated. This is done by connecting the two nose pieces and sending a signal from the sound emitter unit 12 along the tube 17 past the microphone 31 in the termination piece 27, through the two nose pieces 29–30 to the microphone 32 in the other adaptation piece 28. The run time for the sound signal from the one microphone 31 to the other microphone 32 is hereinafter determined and equals then a zero length of the nose separation.

When the nose adaptation pieces hereinafter are mounted at the patient's 46 two nostrils, the sound impulse propagates up into the nose, behind the nose separation to the second nose adaptation piece 30 and the termination piece 28 with the microphone 32. The increase of the run time will be an expression of two times the length of the nose separation. A simple calculation (division) with the sound speed gives the desired length.

The advantage by using more alternative methods for determining the length of the nose separation accurately with the same already available equipment increases the accuracy of the measurement and hence the safety. This is very important as the nose separation rear edge often is used as a reference point at nose or sleep apnea operations.

In FIG. 12 a further surprising use of the apparatus according to the invention is illustrated. Here the function of a patient's Eustachian tube can be monitored in a particularly simple and safe manner.

The nose adaptation pieces 29–30 and the termination pieces 27–28 with the microphones 31–32 are removed from the measuring tubes 17–18; a plug is inserted in the end of each termination piece 27–28 and the nose adaptation pieces 29–30 are replaced by ear adaptation pieces 49–50; these are inserted with mounted termination pieces 27–28 with microphones 31–32 in the patient's ears (see FIG. 12). The signal wire 16 from the sound emitter unit 12 and the two microphone wires from the microphones 47–48 are lead to the computer, as usual.

A special transmission tube 51 with nose adaptation piece on the one mounting piece 14 of the sound emitter unit, is mounted on the sound emitter unit 12 and the second connecting piece 15 is closed with the previously mentioned end piece 45.

A broad band spectrum continuous sound signal is applied from the transducers 19–22 in the probe housing 12 to the patient's nostrils. The patient is hereafter asked to perform swallowing or to drink. With a normal functioning ear and Eustachian tube a short term opening of the Eustachian tube will occur during each swallowing.

At opening of the Eustachian tube the sound signal will however propagate through the nose rear part through the Eustachian tube to the middle ear and from there through the tympanic-membrane to the ear adaptation pieces 49–50 and the two microphones 31–32.

At the following signal processing in the computer system it is possible to determine the symmetry in the transmission paths and opening times, and if one of the signal paths is not opened, caused by a malfunction in the Eustachian tube, a cold or middle ear inflammation (otitis media) this will be detected in details by the apparatus according to the invention and give the examiner the possibility of performing additional examinations of the patient.

It is hereby possible, using the same apparatus according to the invention, to measure and detect several different parameters. Often ear problem are in fact caused by nose problems with polyps or mocous membrane problems in the nose. The measurements and/or detections described will therefore provide a valuable supplement to other examinations which are performed anyway.

The examination of children having middle ear problems is an important part of the work in an ear, nose and throat department in a hospital. The examination method according to the invention described here is an alternative, which is very suitable for children due to the considerably reduced discomfort.

According to the invention it is alternatively possible to send the sound signal the other way; a small nose probe (nose adaptation piece) has to be manufactured with microphone, which is inserted into the nose and the sound signal is then applied to the ear adaptation pieces. Instead of these the examiner can however give the patient normally known headphones, e.g. of the "walkman-type", on the ears. Most of these also function satisfactory as dynamic microphones and can therefore also be used as an alternative for the microphone part when the sound is transmitted from the nose to the ears.

In order to give further confidence for a child at such examination, music or speech can be applied to the phones (microphones) for diverting the attention and only interrupt in the moments when the measurements are performed.

Alternatively the signal path can as mentioned be used in the opposite direction, i.e. with the headphones as a sound source and with the microphones in the holder for the nose adaptation piece maintained in the nose. Hereby the signal can be sampled in the nosepiece during swallowing. This gives the advantage that the physician simultaneously can measure whether the right and left tuba function opens symmetrically in the time domain as well as the size. In case the sound does not exit the ear this can be caused a middle ear inflammation or a malfunction in the Eustachian tube and the physician is hereby able to advice alternative examination methods, e.g. tympanometrics.

What is claimed is:

1. An apparatus for measuring cross sections in a patient's right and left nose cavity in the cavity behind the nose separation, and in the patient's throat, and/or for detecting an opening of the patient's Eustachian tube, the apparatus comprising: an electro-acoustic sound emitter, a first transmission tube extending from the emitter to a first termination piece, a first nose piece for connecting the first termination piece to a first nostril of the patient, a proximal microphone located adjacent the emitter and/or a first microphone located in the first termination piece, and a computer for generating electrical signals for the emitter and for sampling and analyzing electrical signals from the first microphone, the apparatus further comprising a releasable second acoustic transmission tube extending from the emitter in an opposite direction to the first acoustic transmission tube, hereby constituting a elongation of said first transmission tube past the emitter.

2. An apparatus according to claim 1, wherein the second transmission tube extends from the emitter to a second termination piece, wherein the apparatus further comprises a second nose piece for connecting to a second nostril of the patient, and wherein the apparatus comprises a second microphone in the second termination piece.

3. An apparatus according to claim 1, wherein the second transmission tube is constituted by or is terminated by a discrete acoustic impedance.

4. An apparatus according to claim 3, wherein the discrete acoustic impedance has the same value as the acoustic impedance of the transmission tubes.

5. An apparatus according to claim 1, characterized in further comprising microphone units for connecting to the patients nostril, the microphone units preferably are constituted by the first and/or the second connecting piece with the first and the second microphone, respectively.

6. An apparatus according to claim 1, characterized in further comprising microphone units for connecting to the patients ears, the microphone units preferably are constituted by the first and/or the second connecting piece with the first and the second microphone, respectively.

7. An apparatus according to claim 1, characterized in that the emitter comprises one or more electro-acoustic transducers, which preferably are connected to the transmission tubes through a discrete acoustic impedance for achieving the correct impedance adaptation in relation to the acoustic impedance of the transmission tubes.

8. A method for measuring cross sections in a patient's right and left nose cavity) in the cavity behind the nose separation and in the throat, the method comprising: emitting a first acoustic signal from a sound emitter, leading the first acoustic signal along two substantially preferably equally long acoustic transmission tubes to respective nostrils of the patient, receiving a second acoustic signal, reflected from the patient's nostril, by means of one or more microphones located in the acoustic transmission tubes, and leading the first and the second acoustic signal to a computer which performs a data analysis of the signals and their differences for achieving an expression for the cross sections of the patients respiratory passages.

9. A method according to claim 8, characterized in that the first acoustic signal as well as the second reflected acoustic signal are sampled by means of one microphone located close to the emitter, preferably adjacent the emitter.

10. A method according to claim 8, characterized in that the second reflected signal and preferably the first acoustic signal, is/are sampled by means of two microphones located in respective transmission tubes, between the sound emitter and the patient's nostrils.

11. A method for determining the length of the nose separation (septum nasi) in a patient, the method comprising: emitting an acoustic signal from a sound emitter, leading the acoustic signal to the patient's first nostril, sampling the acoustic signal through a microphone connected to the patient's second nostril, and determining the time difference from the first nostril to the second nostril.

12. A method for detecting opening of the Eustachian tube in a patient by means of an apparatus according to the invention, the method comprising emitting an acoustic signal from a sound emitter, leading the acoustic signal to the patients nostril, sampling the acoustic signal through one or more microphones connected to one or both ears of the patients, and determining whether the level of the sampled acoustic signal from the microphones exceeds a predetermined value or is changed.

* * * * *